United States Patent [19]

Ramezanian

[11] Patent Number: 5,254,714
[45] Date of Patent: Oct. 19, 1993

[54] HYDROGENATION OF AROMATIC-SUBSTITUTED OLEFINS USING ORGANORUTHENIUM CATALYST

[75] Inventor: Merrikh Ramezanian, Baton Rouge, La.

[73] Assignee: Ethyl Corporation, Richmond, Va.

[21] Appl. No.: 774,797

[22] Filed: Oct. 10, 1991

[51] Int. Cl.$^5$ .................... C07C 69/76; C07C 229/00; C07F 15/00
[52] U.S. Cl. ............................. 560/8; 556/18; 556/136; 560/1; 560/37; 560/104; 560/105; 560/100; 562/494; 562/495; 562/493; 562/496; 564/161; 564/188; 585/269; 585/277
[58] Field of Search ............... 556/18, 136; 560/1, 560/37, 104, 105, 100, 8; 562/494, 495, 496, 493; 585/269, 277; 564/161, 188

[56] References Cited

U.S. PATENT DOCUMENTS

| | | | |
|---|---|---|---|
| 4,517,390 | 5/1985 | Russell et al. | 568/881 |
| 4,605,758 | 8/1986 | Schloemer | 562/418 |
| 4,707,549 | 11/1987 | Fritz et al. | 544/336 |
| 5,118,837 | 6/1992 | Chalk et al. | 560/261 |

OTHER PUBLICATIONS

Ohta et al., J. Org. Chem., vol. 52, pp. 3174–3176 (1987).

Primary Examiner—José G. Dees
Assistant Examiner—Porfirio Nazario
Attorney, Agent, or Firm—Richard J. Hammond

[57] ABSTRACT

A process is disclosed for the enantioselective hydrogenation of olefins of the formula:

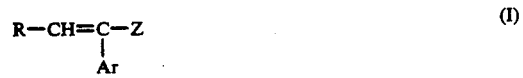

(I)

where R is hydrogen or $C_1$ to $C_6$ linear or branched alkyl, Z is

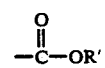

where R' is hydrogen or $C_1$ to $C_6$ linear or branched alkyl, —CN, C(NH)OR" where R" is $C_1$ to $C_6$ linear or branched alkyl, or —C(O)NH$_2$; and Ar is phenyl or naphthyl unsubstituted or substituted with benzoyl or substituted benzoyl, $C_1$ to $C_6$ linear or branched alkyl, $C_1$ to $C_6$ linear or branched alkoxy, halo, or carboxylic acid or $C_1$ to $C_6$ linear or branched alkyl ester thereof, which comprises contacting said aromatic-substituted olefin with a catalytically effective amount of a ruthenium phosphite complex.

10 Claims, No Drawings

HYDROGENATION OF AROMATIC-SUBSTITUTED OLEFINS USING ORGANORUTHENIUM CATALYST

FIELD OF THE INVENTION

This invention relates to a process for the catalytic reduction of aromatic-substituted olefins. More specifically, this invention relates to a process for asymmetrically, catalytically reducing aromatic-substituted olefins using organoruthenium phosphines.

BACKGROUND OF THE INVENTION

Enantioselective catalysis using chiral metal complexes provides one of the most general and flexible methods for achieving asymmetric organic reactions. Metallic elements possess a variety of catalytic activities, and permutations of organic ligands or other auxiliary groups directing the steric course of the reaction are practically unlimited. Efficient ligands must be endowed with, for example, suitable functionality, an appropriate element of symmetry, substituents capable of differentiating space either electronically or sterically and skeletal rigidity or flexibility.

Among the asymmetric organic reactions catalyzed by chiral transition metal complexes, asymmetric hydrogenation has been one of the best studied, due in large part to the fact that it is the basis for the first commercialized catalytic asymmetric process. See, for example, ApSimon, et al., *Tetrahedron*, 1986, 42, 5157.

Some of the more interesting of the asymmetric hydrogenation catalysts are those derived from BINAP [2,2'-bis(diphenyl-phosphino)- 1,1'-binaphthyl]. See, for example, U.S. Pat. Nos.: 4,691,037; 4,739,084; 4,739,085; and 4,766,227. Unlike the more classical models of chiral (asymmetric) molecules, chirality in the case of the BINAP compounds arises from the restricted rotation about the single bond joining the naphthalene, i rings. Because of such restricted rotation, perpendicular disymmetric planes result. Isomers arising from this type of asymmetry are termed atropisomers.

Cationic rhodium-BINAP complexes have been shown to catalyze the isomerization of allylamines to chiral enamines in 94-96% ee. Also, hydrogenations of geraniol and nerol (bis-unsaturated alcohols) using rhodium-BINAP complexes produce products in about 50% eels. The synthesis of BINAP derivatives bearing groups other than phenyl on phosphorus such as paramethylphenyl and cyclohexyl have also been prepared. Inoue, et al., *Chem. Lett.*, 1985, 1007.

Studies on the mechanism of rhodium-phosphine catalyzed asymmetric reductions of α,β-unsaturated acids or esters bearing an α-acetamido group have shown that the reaction proceeds by the displacement of solvent by the unsaturated substrate forming a chelate complex in which the olefin and the carbonyl oxygen of the acetamido function are bound to the metal. See Halpern, J., *Asymmetric Synthesis*, Vol. 5, pp. 41–69, J. D. Morrison, Ed., Academic Press, Inc., 1985. Substrates lacking the α-acetamido group are reduced with far less stereoselectivity. α,β and β,γ-unsaturated amides similarly form complexes in which the olefin and carboxamide oxygen are bound to rhodium. These reactions proceed with high stereoselectivity. See Brown, et al, *J. Org. Chem.*, 47, 2722 (1982) and Koenig, K. E., Asymmetric Synthesis, Vol. 5, pp. 71–101, J. D. Morrison, Ed., Academic Press, Inc., 1985.

The BINAP ruthenium complexes are dramatically different than the rhodium ones. They have been used to catalyze a variety of asymmetric hydrogenations, including the hydrogenation of enamides and alkyl and aryl-substituted acrylic acids. See Noyori, et al., *Modern Synthetic Methods*, 1989, 5, 115, incorporated herein by reference.

However, unlike the rhodium catalyzed reductions, ruthenium (II) carboxylate complexes possessing the BINAP ligand are efficient catalysts for the enantioselective transformation of α,β-unsaturated carboxylic acids. Amide-bearing olefins as well as carboxylic acid esters are essentially unreactive with these catalysts. According to Ohta, et al, J. Org. Chem, 52, 3174 (1982), the carboxylate moiety, and not other oxygen containing groups, is responsible for the stereoselective reaction. Noncarboxylate-containing substrates are unaffected by ruthenium complexes in these asymmetric reductions.

SUMMARY OF THE INVENTION

The present invention involves a novel method for the use of organoruthenium-carboxylate catalysts which, when comprised of ligands having optical activity, can be used as the catalyst for effecting the asymmetric reduction of certain unsaturated organic compounds.

DESCRIPTION OF THE PREFERRED EMBODIMENTS

The process of the present invention involves the enantioselective hydrogenation (reduction) of aromatic-substituted olefins of the formula:

where R is hydrogen or $C_1$ to $C_6$ linear or branched alkyl; Z is selected from the group

where R' and R" are the same or different and are $C_1$ to $C_6$ linear or branched alkyl; and Ar is phenyl or naphthyl unsubstituted or substituted with benzoyl or substituted benzoyl, $C_1$ to $C_6$ linear or branched alkyl, $C_1$ to $C_6$ linear or branched alkoxy, halo (chloro, bromo, iodo or fluoro), or carboxylic acid or the carboxylic acid alkyl esters thereof. The term "substituted" as used herein means a benzoyl group having at least one substituent (ortho, nitro or para) such as halo, amino, nitro, hydroxy, $C_1$ to $C_6$ linear or branched alkyl or $C_1$ to $C_6$ linear or branched alkoxy.

In the above olefins, it is preferred that R is hydrogen, methyl or ethyl; R' and R" are the same and are methyl or ethyl; and Ar is phenyl or naphthyl unsubstituted or substituted with benzoyl, methyl, isobutyl, methoxy, chloro or fluoro. Most preferably R is hydrogen, R' and R" are the same and are methyl or ethyl and Ar is phenyl substituted with isobutyl or naphthyl substituted with methoxy.

None of the above compounds, including the preferred compounds as well as the most preferred compounds, are novel, their preparation being illustrated by the reaction schemes set out below:

1) For R—CH=C—Z   where Z is —CN.
         |
         Ar

See Neway et al., *J. Amer. Chem. Soc.*, 72 5645 (1950).

2) For RCH=C—Z   where Z is —C(O)NH$_2$.
         |
         Ar

See U.S. Pat. Nos. 3,478,105, and 3,816,443.

3) For RCH=C—Z   where Z is —C(O)OR".
         |
         Ar

See Villieras et al., *Synthesis*, 1984, 406-8 and Seitz et al., West German Patent DE 3317356.

The asymmetric reduction process of the present invention employs a catalyst that, as noted herein, is a ruthenium phosphorus complex. It has the formula:

$$Ru_xH_yCl_z(R^4-D-3PE)_2(S)_p \quad (III)$$

where $R^4$—D—3PE signifies a tertiary phosphine of the formula:

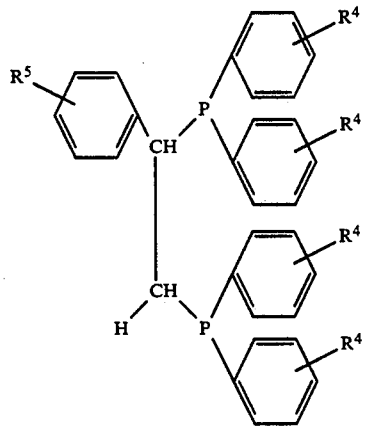

(III)

where $R^4$ is a hydrogen, methyl or methoxy group; $R^5$ is hydrogen or $C_1$ to $C_9$ linear or branched alkyl; S is a tertiary amine; when y is 0, then x is 2, z is 4 and p is 1; and when y is 1, then x is 1, z is 1 and p is 0, as well as those having the formula:

$$[Ru(R^4-D-3PE)_q\overset{O}{\underset{\|}{O}}C-R^6]O\overset{O}{\underset{\|}{C}}R^7 \quad (IV)$$

where $R^4$—D—3PE is as previously described; $R^5$ represents a hydrogen atom or alkyl group having from 1 to 9 linear or branched carbon atoms, a halogenated alkyl group having from 1 to 4 linear or branched carbon atoms (examples of the halogen include fluorine, chlorine and bromine), a phenyl group, a phenyl group substituted at positions 2, 3 or 4 with an alkyl group having from 1 to 4 linear or branched carbon atoms, and α-aminoalkyl group (e.g., those having from 1 to 4 linear or branched carbon atoms), or an α-aminophenylalkyl group (e.g., those having from 7 to 10 linear or branched carbon atoms), or $R^6$ and $R^7$ are taken together to form an alkylene group having from 1 to 4 linear or branched carbon atoms; and q represents 1 or 2; or $$[RuH_t(R^4-D-3PE)_v]Y_w \quad (V)$$

where $R^4$ —D—3PE is as previously described; Y is [S$_2$CN(CH$_3$)$_2$], (O$_2$CCH$_3$), (NCS) or [(R$_1$)C(O)CH$_2$(R$_2$)C(O)] where $R_1$ and $R_2$ are the same or different and are hydrogen or $C_1$ to $C_6$ linear or branched alkyl; when t is 0, then v is 1 and w is 2; and when t is 1, then v is 2 and w is 1.

It should be noted that $R^4$—D—3PE (sometimes referred to in this specification as $R^4$-DPPPE) is an abbreviation for the group 1,2-bis(diphenylphosphino)-phenylethane, where one or more $R^4$ substituents, such as hydrogen, methyl, ethyl and the like, are attached to the phenyl-phosphorus moiety and one or more $R^5$ substituents, e.g., hydrogen, methyl, ethyl and the like, are attached to the phenyl-methylene moiety. (See compound III.)

The ruthenium-optically active phosphine complex of formula (II) can be obtained by the methods referenced in Ohta, et al, ibid, or as further described in Ikariya, et al, *J. Chem. Soc., Chem. Commun.*, pp. 922-924 (1985) as well as in European Patent No. 174,057A and European Patent Application No. 87310023.4, all of which are incorporated in their entirety by reference herein. Specific examples of the optically active ruthenium phosphine complex are:

Ru$_2$Cl$_4$ (D-3PE)$_2$(NEt$_3$);
Ru$_2$Cl$_4$(BINAP)$_2$(NE4)$_3$, where $R^4$ is methyl and $R^5$ is hydrogen;
RuHCl (D-3PE)$_2$;
RuHCl (D-3PE)$_2$;
Ru(D-3PE) (O$_2$CCH$_3$)$_2$;
Ru(D-3PE) (O$_2$CCF$_3$)$_2$;
Ru(D-3PE) (O$_2$CPh)$_2$; and
D-3PE[(CH$_3$)C(O)CH$_2$(CH$_3$)C(O)].

As noted earlier, the above catalysts are useful in stereoselective hydrogenation of olefinic compounds of the formula:

$$R-CH=\underset{\underset{Ar}{|}}{C}-Z \quad (I)$$

where R, Z and Ar are defined above. Solutions of these olefins are typically admixed with a catalytically effective amount of the ruthenium complexes and hydrogenated at about 20° C. to about 100° C. under about 20 to about 1000 psi of hydrogen.

EXAMPLES

The present invention is described in greater detail by reference to the following non-limiting Examples.

EXAMPLE 1

S(+)-1,2-Bis(methanesulphonyloxy)-1-phenylethane (S-BMPE)

To a cooled (−5° C.) solution of S(−)-phenylethane-1,2-diol (3 g, 21.7 mmol) in dry pyridine (15 mL) was added methane-sulphonyl chloride (3.83 mL, 5.63 g, 48.7 mmol) by syringe over 1 hour while the temperature was maintained at −5° C. with stirring. The thick white suspension was stirred for 4 hours at 0° C., then poured onto ice (50 g), mixed well, and acidified to pH 3 with concentrated HCl. The mixture was filtered, washed with water (2×20 mL), and the wet solid was dissolved in dichloromethane (40 mL). The aqueous layer was extracted with dichloromethane (2×5 mL). These organic extracts were combined with the dissolved residue from above, dried (MgSO4), filtered and hexane (25 mL) was added to the filtrate. This solution was kept in a refrigerator overnight. A white crystalline solid (5.29, 81%) was obtained by filtration. m.p. 109°–111° C.; $[\alpha]^{10} -87.6°$ (in CHCl3); $^1$H-NMR: δ2.86 (s, 3H, CH3), 3.08 (s, 3H, CH3), 4.42, (dd, J=12.1, 3.6 Hz, 1H, CH2), 4.54 (dd, J=12.1, 8.1 Hz, 1H, CH2), 5.81 (dd, J=8.1, 3.6 Hz, 1H, CH3O, 7.28–7.52 (m, 5H, ArH).

EXAMPLE 2

R(−)-1, 2-Bis(diphenylphosphino)phenylethane (R-DPPPE)

To a cooled (10° C.), degassed solution of diphenylphosphine (2.6 g, 13.96 mmol) in THF (20 mL) was added dropwise degassed butyllithium (2.5 M in hexane, 6.5 mL, 13.96 mmol) with stirring. The mixture was stirred at RT for 1 hour and then cooled to −78° C. To this cold, dark red solution was added dropwise a degassed solution of S(+)-phenylethylene-1,2-bis-methanesulphonate (S-BMPE) (1.9 g, 6.5 mmol) in THF (20 mL). This mixture was allowed to warm to RT with stirring. A colorless slurry was obtained, which upon removal of solvent under reduced pressure gave a solid residue. The residue was stirred with degassed methanol (50 mL) for 0.5 hour and a white solid was filtered. Recrystallization under argon from a degassed mixture of dichloromethane (20 mL) and methanol (20 mL) gave R(−)-1,2-bis(diphenylphosphino)phenylethane (R-DPPPE) as fine, white crystals (2.1 g, 70%). m.p. 165°–170° C. (dec.); $[\alpha^{20} -36.2°$ (in CHCl3); $^1$H-NMR: δ 2.40–2.62 (m, 2H, CH2), 3.24–3.36 (m, 1H, CH), 6.31–7.45 (m, 25H, ArH) $^{31}$p-NMR: δ3.6, −21.4.

EXAMPLE 3

R(−)-1,2-Bis(diphenylphosphino)phenylethane Ruthenium(II) Bis(dimethyldithiocarbamate) [(R-DPPE)Ru(S2CNMe2)2]

Degassed DMF (1 mL) was added to a mixture of cyclooctadiene ruthenium(II)dimethyldithiocarbamate, [(COD)Ru(S2CNMe2)], (42 mg, 0.1 mmol) and R(−)-1,2-bis(diphenylphosphino)phenylethane (R-DPPPE) (56.88 mg, 0.12 mmol) under argon with stirring. The resulting green solution was heated to 130°–135° C. for 20 hours. Solvent was removed to give a greenish yellow solid. Recrystallization from dichloromethane/hexane (1:20) gave a yellow powder (200 mg, 60%). $^1$H-NMR: δ2.70, 2.85, 2.88, 3.20 (s, 6H, CH3), 3.3 (m, 2H, CH2), 6.70–7.92 (m, 25H, ArH); $^{31}$p-NMR: δ58.0, 87.4, 89.8.

EXAMPLE 4

R(−)-1,2-Bis(diphenyphosphino)phenylethane Ruthenium(II) Diacetylacetone [(R-DPPPE)Ru(acac)2]

Degassed DMF (3 mL) and pyridine (300 mg, 0.306 mL) were added to a mixture of cyclooctadiene ruthenium(II) diacetylacetone (84 mg, 0.21 mmol) and R-DPPPE (109 mg, 0.23 mmol) at RT under nitrogen with stirring. This was heated to 140° C. for 20 hours, and then the solution concentrated under reduced pressure. Recrystallization from dichloromethane hexane gave orange crystal (348 mg, 70%). $^1$H-NMR: δ1.41–1.69 (m, 12H, CH3), 3.85 (m, 2H, CH2), 4.15 (m, 1H, CH), 4.64 (d, J=6.1 Hz, 2H, CH2), 6.70–8.20 (m, 25H, ArH $^{31}$p-NMR: δ63.4, 65.4 (CHP), 91.9, 97.0 (CH2P).

EXAMPLE 5

R(−)-1,2-Bis(diphenylphosphino)phenylethane Ruthenium(II) Diacetate [(R-DPPPE)Ru(OAc)2]

To a mixture of [RuCl2(COD)]n (279.6 mg, 1 mmol) and R-DPPPE (512 mg, 1.08 mmol) placed in a 100 mL flask under argon were added dry, degassed toluene (35 mL) and triethylamine (0.6 mL, 4.24 mmol). Reaction was complete after 3 hours refluxing at 115–120° C. The resulting mixture was cooled to RT, and the solvent was removed under reduced pressure to leave a brown solid. This was dissolved in dry degassed dichloromethane (25 mL). After filtration, the filtrate was concentrated under vacuum. A brown solid was obtained. To the residue was added anhydrous sodium acetate (436 mg, 5.42 mmol) and degassed t-BuOH (55 mL). The mixture was stirred at reflux for 16 hours. A brown precipitate was obtained. The solvent was removed under vacuum and the resulting solid was extracted with ether (2×15 mL), and combined extracts were evaporated under reduced pressure to give a light brown solid. This solid was extracted with absolute ethanol (2×15 mL). Removal of the solvent afforded a brown solid (774 mg). Recrystallization from dichloromethane/hexane gave dark brown crystals (550 mg, 80%). $^1$H-NMR: δ6 2.08 (b, 6H, CH3), 3.2 (m, 2H, CH2), 4.22 (m, 1H, CH), 6.5–7.7 (m, 25H, ArH) $^{31}$p-NMR: δ40.8, 66.5,

EXAMPLE 6

R(−)-1,2-Bis(diphenylphosphino)phenylethane Nickel(II)-dithiocyanate [(R-DPPPE)Ni(SCN)2]

A slurry of R-DPPPE (474 mg, 1 mmol) in ether (20 mL) was added dropwise to the green solution of nickel perchlorate hexahydrate (250 mg) and sodium thiocyanate (250 mg) in ethanol (5 mL) with stirring under nitrogen. After stirring overnight at RT, the yellow solid was collected, washed with ethanol (2×2.5 mL) and ether (2×2 mL) to give product (450 mg, 70%). $^1$H-NMR: δ2.60 (m, 2H, CH2), 3.75 (m, 1H, CH), 6.55 (d, J=7.3 Hz, 2H), 7.05 (t, J=7.3 Hz, 2H), 7.19 (m, 1H), 7.42–7.86 (m, 18H), 8.35 (m, 2H); $^{31}$p-NMR: δ41.3, 41.9, 68.8, 69.5.

EXAMPLE 7

R(−)-1,2-Bis(diphenylphosphino)phenylethane Nickel(II) Diacetate [(R-DPPPE)Ni(OAc)2]

A solution of R-DPPPE (237 mg, 0.5 mmol) in ether (20 mL) was added to a green solution of nickel diacetate tetrahydrate (373.5 mg, 1.5 mmol) in ethanol (10 mL) under nitrogen with stirring. The color changed to yellow and then to reddish brown. After 3 days stirring, a yellow solid was obtained. After filtration, the solid was washed with ethanol and then ether to give product (120 mg, 37%). $^1$H-NMR: δ4.22 (b, 1H, CH), 2.71 (b, 2H, CH2), 6.81–8.12 (b, 25H, ArH) ; $^{31}$p-NMR: 3.9, 4.2, 30.2, 30.5.

Hydrogenations with Preformed Catalysts

The catalyst of the present invention and 2-(4-isobutylphenyl)acrylic acid (UA) were weighed out and combined in a 25-mL flask in a nitrogen-filled glove box. The mixture was transferred to the high pressure reactor using 30-50 mL of solvent. The reactor was flushed with $H_2$ (3×300 psi) and then sealed under $H_2$. The mixture was stirred (300-700 rpm) under the conditions shown in Table I. All reductions were carried out at 900-1000 psi $H_2$ pressures.

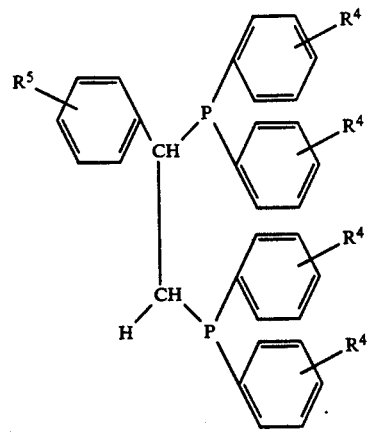

(III)

TABLE I

| EXAMPLE | SUBSTRATE (mmol)/ REACTOR CONSTR.* | CATALYST STOICHIOMETRY (mmol) | | SOLVENT | TEMP/TIME (°C./hr) | CONVERSION (GC Area %) | % ee |
|---|---|---|---|---|---|---|---|
| | | METAL COMPLEX | PHOSPHINE LIGAND | | | | |
| 8 | UA(1.25)/SS | Ru(acac)₃ (0.048) | R-DPPPE (0.057) (From Example 2) | in situ<sup>a</sup> MeOH | 22/16.5 60/24 | 0 100 | 20(S) |
| 9 | UA(1.35)/SS | Ru(R-DPPPE)(OAc)₂ (0.045) (From Example 5) | None | MeOH | 21/16 | 100 | 10(S) |
| 10 | UA(1.26)/SS | Ru(R-DPPPE)(acac)₂ (0.043) (From Example 4) | None | MeOH | 22/20 | 81 | 16(S) |
| 11 | UA(1.43)/SS | Ru(R-DPPPE)(S₂CNMe₂)₂ (0.015) (From Example 3) | None | MeOH | 21/22 101/16 | 0 6 | 93(S) |
| 12 | UA(1.34)/SS | Ru(R-DPPPE)(S₂CNMe₂)₂ (0.039) (From Example 3) | None | MeOH | 60/7 100/24 | 0 9 | 89(S) |

<sup>a</sup>Catalyst components in methanol were treated with $H_2$ (60° C./1000 psi/3 hr) before introducing substrate.
*Reactor construction: SS = 316 Stainless Steel.

What is claimed is:

1. A process for the enantioselective hydrogenation of an aromatic-substituted olefin of the formula:

$$R-CH=C-Z \atop |\atop Ar \qquad (I)$$

where R is hydrogen or $C_1$ to $C_6$ linear or branched alkyl, Z is $$-\overset{O}{\underset{\|}{C}}-OR'$$

where R' is hydrogen or $C_1$ to $C_6$ linear or branched alkyl, —CN, C(NH)OR" where R" is $C_1$ to $C_6$ linear or branched alkyl, or —C(O)NH₂; and Ar is phenyl or naphthyl unsubstituted or substituted with benzoyl or substituted benzoyl, $C_1$ to $C_6$ linear or branched alkyl, $C_1$ to $C_6$ linear or branched alkoxy, halo, or carboxylic acid or $C_1$ to $C_6$ linear or branched alkyl ester thereof, which comprises contacting said aromatic-substituted olefin with a catalytically effective amount of a ruthenium phosphite complex of the formula:

$$[Ru(R^4-D-3PE)_q\overset{O}{\underset{\|}{OC}}-R^6]\overset{O}{\underset{\|}{OCR^7}}$$

where $R^4$—D—3PE is $R^5$ represents a hydrogen atom or alkyl group having from 1 to 9 linear or branched carbon atoms, a halogenated alkyl group having from I to 4 linear or branched carbon atoms, a phenyl group, a phenyl group substituted with an alkyl group having from 1 to 4 linear or branched carbon atoms, and α-aminoalkyl group, the alkyl group having from 1 to 4 linear or branched carbon atoms, or an a-aminophenylalkyl group, the alkyl group having from 7 to 10 carbon atoms, or $R^6$ and $R^7$ are taken together to form an alkylene group having from I to 4 linear or branched carbon atoms; and q represents 1 or 2.

2. The process according to claim 1 where R is hydrogen or methyl or ethyl, R' and R" are the same and are methyl or ethyl and Ar is phenyl or naphthyl unsubstituted or substituted with benzoyl, methyl, isobutyl, methoxy, chloro or fluoro.

3. The process according to claim 2 where R' and R" are the same and are methyl or ethyl and Ar is phenyl substituted with isobutyl or naphthyl substituted with methoxy.

4. The process according to claim 3 where R is hydrogen.

5. The process according to claim 4 where Z is

6. A process for the enantioselective hydrogenation of an aromatic-substituted olefin of the formula:

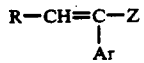

where R is hydrogen or $C_1$ to $C_6$ linear or branched alkyl, Z is

where R' is hydrogen or $C_1$ to $C_6$ linear or branched alkyl, —CN, C(NH)OR" where R" is $C_1$ to $C_6$ linear or branched alkyl, or —C(O)NH$_2$; and Ar is phenyl or naphthyl unsubstituted or substituted with benzoyl or substituted benzoyl, $C_1$ to $C_6$ linear or branched alkyl, $C_1$ to $C_6$ linear or branched alkoxy, halo, or carboxylic acid or $C_1$ to $C_6$ linear or branched alkyl ester thereof, which comprises contacting said aromatic-substituted olefin with a catalytically effective amount of a ruthenium phosphite complex of the formula:

$$[RuH_t(R^4—D—3PE)_v]Y_w \quad (V)$$

where $R^4$—D—3PE is

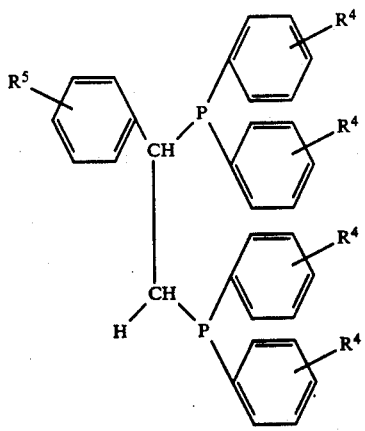

Y is [S$_2$CN(CH$_3$)$_2$, (O$_2$CCH$_3$), (NCS) or [(R$_1$)C(O)CH$_2$(R$_2$)C(O)] where R$_1$ and R$_2$ are the same or different and are hydrogen or $C_1$ to $C_6$ linear or branched alkyl; when t is 0, then v is 1 and w is 2; and when t is 1, then v is 2 and w is 1.

7. The process according to claim 6 where R is hydrogen or methyl or ethyl, R' and R" are the same and are methyl or ethyl and Ar is phenyl or naphthyl unsubstituted or substituted with benzoyl, methyl, isobutyl, methoxy, chloro or fluoro.

8. The process according to claim 7 where R' and R" are the same and are methyl or ethyl and Ar is phenyl substituted with isobutyl or naphthyl substituted with methoxy.

9. The process according to claim 8 where R is hydrogen.

10. The process according to claim 9 where Z is